United States Patent [19]

Paciorek et al.

[11] 4,024,067
[45] May 17, 1977

[54] PROCESSES FOR THE PREPARATION OF BIS-BENZOINS AND BIS-BENZILS

[75] Inventors: Kazimiera J. L. Paciorek, Corona del Mar; Reinhold H. Kratzer, Costa Mesa; Dennis W. Karle, Mission Viejo, all of Calif.

[73] Assignee: The United States of America as represented by the Secretary of the Navy, Washington, D.C.

[22] Filed: Jan. 7, 1976

[21] Appl. No.: 647,038

[52] U.S. Cl. .......................... 260/590 D; 260/592; 260/63 N; 260/250 Q
[51] Int. Cl.$^2$ ........................................ C07C 49/82
[58] Field of Search ....... 260/590 D, 590 E, 590 R, 260/592

[56] References Cited
UNITED STATES PATENTS

| | | | |
|---|---|---|---|
| 3,498,981 | 3/1971 | Culbertson | 260/590 R |
| 3,595,922 | 7/1971 | Manos | 260/590 R |

OTHER PUBLICATIONS

Biquard, Chem. Abst., vol. 26, pp. 3787 (1932).
Kuebrich et al., J.A.C.S., vol. 93:5, pp. 1220–1223 (1971).
Morrison et al., Organic Chemistry, pp. 638–639 (1967).
Kuebrich et al., J.A.C.S., vol. 93:5, pp. 1214–1220 (1971).
Wiberg, J. Org. Chem., vol. 76, pp. 5371–5375.

*Primary Examiner*—James O. Thomas, Jr.
*Assistant Examiner*—James H. Reamer
*Attorney, Agent, or Firm*—R. S. Sciascia; A. L. Branning; R. D. Johnson

[57] ABSTRACT

Bis-benzoins of the formula

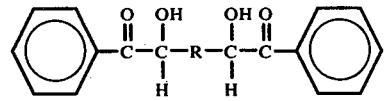

wherein R is meta-phenylene or para-phenylene are prepared by first contacting aldehydes of the formula

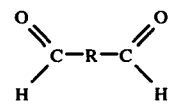

with sodium bisulfite to form bisulfite addition products of the formula

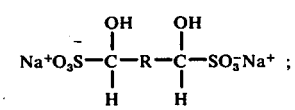

then contacting the bisulfite addition products with either potassium cyanide or sodium cyanide to form cyanohydrins of the formula

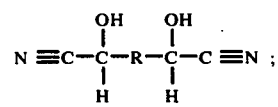

and finally contacting the cyanohydrins with benzaldehyde to form the bis-benzoins. The bis-benzoins can be oxidized to form the corresponding bis-benzils which are useful as starting materials for producing phenylated polyquinoxalines which in turn are useful as coatings for fibers, graphite precursors, films and laminating materials.

2 Claims, No Drawings

PROCESSES FOR THE PREPARATION OF BIS-BENZOINS AND BIS-BENZILS

BACKGROUND OF THE INVENTION

This invention relates generally to aromatic ketones and more specifically to bis-benzoins.

Poly[2,2'-(1,4-phenylene)-6,6'-bis(3-phenylquinoxaline)] and poly[2,2'-(1,3-phenylene)-6,6'-bis(3-phenylquinoxaline)] are useful as coatings for fibers, graphite precursors, films and laminating materials. These polymers possess two excellent properties: high thermal stability and good solubility in many organic solvents. This second property permits coatings of these polymers to be applied without heat curing. Further, it permits components coated with these polymers to be inspected by desolving the coating with ordinary organic solvents.

The above-mentioned polymers are synthesized by reacting 3,3'-diaminobenzidine with either 1,4-bis(-phenylglyoxaloyl) benzene, i.e., p-phenylglyoxyloyl benzil, or with 1,3-bis(phenylglyoxaloyl) benzene, i.e., m-phenylglyoxyloyl benzil, by the method disclosed by W. Wrasidlo and J. M. Augl in "Phenylated Polyquinoxalines from Bis(phenylglyoxaloyl)Benzene," Journal of Polymer Science: Part A-1 Volume 7 (1965) PP. 3393–3405. This article also discloses a method of preparing the 1,4-bis(phenylglyoxaloyl) benzene and 1,3-bis(phenylglyoxalyl) benzene. Likewise, articles by J. Schmitt et al, Bull Soc. Chim. France, 636 (1956), and M. A. Ogliaruso and E. I. Becker, J. Org. Chem. 30, 3354 (1965) disclose methods which may be used to prepare these bis-α-diketones. Unfortunately, these prior art processes produce the bis-α-diketones in low yields using expensive starting materials or many separate reaction steps. Moreover, in many cases the product bis-α-diketones can only be purified with difficulty.

SUMMARY OF THE INVENTION

Accordingly, it is an object of this invention to provide a process for preparing 1,3-and 1,4-bis(phenylgloxaloyl) benzenes from inexpensive starting materials.

It is another objective of this invention to provide a process by which 1,3- and 1,4-bis(phenylgloxaloyl) benzenes may quickly and easily be prepared.

A further object of this invention is to provide a process by which higher yields of 1,3- and 1,4-bis(-phenylgloxaloyl) benzenes can be obtained.

Yet another object of this invention is to provide a process in which the product 1,3- and 1,4-bis(phenylgloxaloyl) benzenes can easily be purified.

Yet a further objective of this invention is to provide novel compounds.

Still another objective of this invention is to provide a process for preparing novel chemical compounds.

These and other objects of this invention are accomplished by providing bis-benzoins of the formula

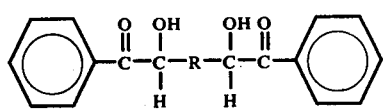

wherein R is meta-phenylene or para-phenylene which are easily oxidized to form the corresponding bis-benzils of the formula:

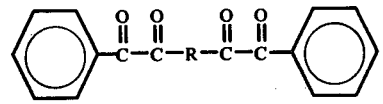

when R is meta-phenylene the bis-benzil is 1,3-bis(-phenylglyoxaloyl) benzene, and when R is para-phenylene the bis-benzil is 1,4-bis(phenylglyoxaloyl) benzene. These bis-benzils are starting materials for the production of poly[2,2'-(1,3-phenylene)-6,6'-bis(3-phenylquinoxaline)] and poly[2,2'-(1,4-phenylene)-6,6'- bis(3-phenylquinoxaline)]; these polymers are useful as coatings for fibers, graphite precursors, films and laminating materials.

DETAILED DESCRIPTION OF THE PREFERRED EMBODIMENT

The reaction sequences for the present invention can be summarized as follows:

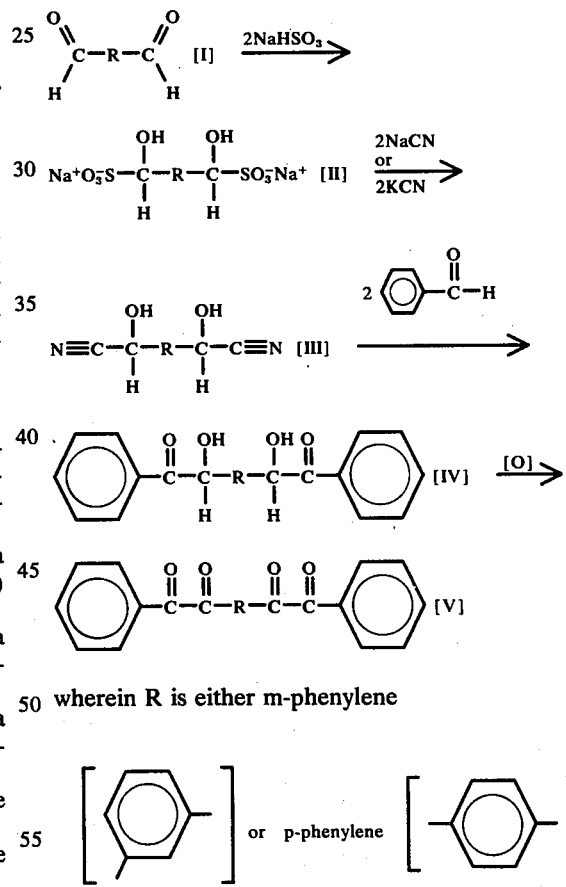

wherein R is either m-phenylene

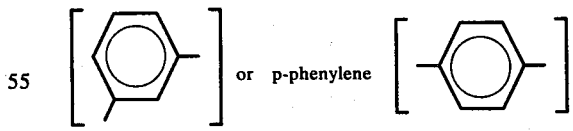

or p-phenylene.

The bis-benzoins are prepared by first contacting aldehydes of the formula

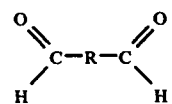

with sodium bisulfite to form bisulfite addition products of the formula

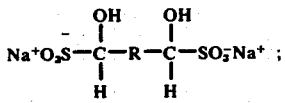

then contacting the bisulfite addition products with a cyanide selected from the group consisting of sodium cyanide and potassium cyanide to form cyanohydrins of the formula

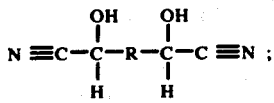

and finally contacting the cyanohydrins with benzaldehyde to form the bis-benzoin of the formula

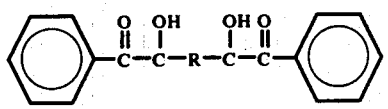

wherein R is selected from the group consisting of meta-phenylene and para-phenylene.

For R equal to m-phenylene, isopthalaldehyde,

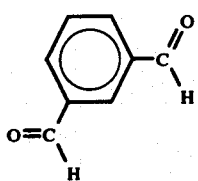

is used as the starting material (I), but for R equal to p-phenylene, terephthalaldehyde

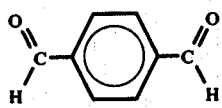

is used.

The first reaction step involves the normal addition of a bisulfite to an aldehyde. This can be accomplished by bringing the aldehyde into contact with an aqueous solution of sodium bisulfite at ambient temperatures to produce the bisulfite addition product (II). Two moles of sodium bisulfite react with each mole of the dialdehyde (I).

The reaction between the bisulfite addition product (II) and sodium cyanide or potassium cyanide may be conveniently run in water. The water should be stirred to maintain a suspension of the bisulfite addition product. The reaction mixture should be cooled, preferably to a temperature in the range of from 0° to about 10° C. The sodium cyanide or potassium cyanide, preferably dissolved in water, is slowly added to the reaction mixture. Two moles of sodium cyanide or potassium cyanide react with each mole of the bisulfite addition product.

The reaction mixture, containing the cyanohydrin (III) as well as inorganic reaction by-products, is slowly added to at least two moles of benzaldehyde for each mole of cyanohydrin in solution. During this step, the reaction temperature is preferably kept between 10° and 90° C. After the addition is completed the cyanohydrin-water-benzaldehyde is kept at this temperature until the reaction is completed; usually this takes only a few hours. During this step two moles of benzaldehyde react with each mole of cyanohydrin (III) to form the bis-benzoin (IV).

Benzoins oxidize easily to form benzils. In the present invention, mild oxidation of the bis-benzoin (V) produces the corresponding bis-benzils. For instance, examples I and II use cupric acetate and ammonium nitrate with 80% acetic acid as the solvent. See Weiss and Appel, J.A.C.S. 70, 3666 (1948). Phil Manos in U.S. Pat. No. 3,595,922 entitled "Benzil Preparation," discloses a method of oxidizing benzoins to benzils using cupric carboxylate in catalytic amounts, a solvent selected from the group consisting of acetic acid and water-miscible alcohols, and a gas containing oxygen molecules which is bubbled through the reaction mixture. Other state of the art methods may also be used.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLE I

To a stirred suspension of terephthalaldehyde-bid-sodium bisulfite adduct (10.0 g, 0.0292 mol) in water (30 ml), cooled in an ice bath, was added a solution of potassium cyanide (2.96 g, 0.0584 mol) in water (15 ml) over a period of 27 min. The aqueous solution of the thus prepared cyanohydrin (which also contained the inorganic reaction by-products) was then added to stirred benzaldehyde (62 g, 0.584 mol) at 56°–63° C over a period of 10 min. Subsequently the reaction mixture was stirred at 55°–77° C for 1 hr 15 min. After cooling, water (250 ml) was added and the mixture was extracted with ether (250 ml). The ethereal solution, following washing with water and drying over magnesium sulfate, on evaporation gave a solid (11.68 g). This material was subsequently dissolved in 80% acetic acid (140 ml) and heated with stirring at 101°–105° C together with ammonium nitrate (20 g, 0.2498 mol) and cupric acetate (0.2g). On cooling yellow crystals of p-phenylglyoxyloyl benzil, i.e., 1,4-bis(phenylglyoxaloyl)benzene, $C_6H_5C(O)C(O)C_6H_4C(O)C(O)C_6H_5$ (6.39 g. 63.5% yield), mp 119°–124° C appeared. Crystallization from ethanol gave pure product (5.13 g, 51% yield) mp 123.5°–124.2° C.

EXAMPLE II

The terephthalaldehyde cyanohydrin was prepared (in a manner analogous to that as described for Example I) in two batches each using 42.8 g (0.1451 mol) of sodium bisulfite adduct, 17.0 g (0.2611 mol) of potassium cyanide and 320 ml of water. The addition of the thus produced cyanohydrin to the preheated (69° C) benzaldehyde (553 g, 5.214 mol) was conducted under nitrogen by-pass. The first batch was added in approximately 22 min; the second in approximately 14 min. Subsequently the reaction mixture was heated with stirring for 2 hr. at 68°–73° C. After cooling the insoluble material (6.6 g) was filtered off. A small portion of this material was extracted with acetonitrile and crystallized from this solvent giving pure 1,4-bis benzoin, $C_6H_5C(O)CH(OH)C_6H_4CH(OH)C(O)C_6H_5$, mp 230°–233° C.

Anal. Calcd for $C_{22}H_{18}O_4$: C, 76.29%; H, 5.24%; O, 18,48%. Found: C, 75.88%; H, 5.29%.

The original filtrate was separated into organic and aqueous layers. The organic phase was evaporated in vacuo at 80°–90° C to remove the excess benzaldehyde giving a solid mass (157.3 g). This material (157.2 g) was combined with the insoluble portion filtered off above and dissolved in 80% acetic acid (1,400 ml) and the solution was stirred at 100°–108° C with ammonium nitrate (200 g) and cupric acetate (4.0 g) for 5 hr. On cooling yellow crystals of p-phenylglyoxyloyl benzil, i.e., 1,4-bis(phenylgloxaioyl) benzene, (88.0 g, mp 117°–119° C) were formed. Crystallization from acetic acid gave pure product (50.0 g, 50% yield) mp 122.5°–123.5° C.

Obviously, numerous modifications and variations of the present invention are possible in light of the above teachings. It is therefore understood that within the scope of the appended claims the invention may be practiced otherwise than as specifically described herein.

What is claimed as new and desired to be secured as Letters patent of the United States is:

1. A bis-benzoin having the formula

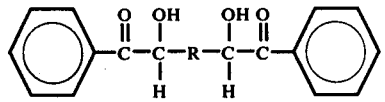

wherein R is selected from the group consisting of meta-phenylene and para-phenylene.

2. The bis-benzoin of claim 1 wherein R is para-phenylene.

* * * * *